US00PP23604P3

(12) United States Plant Patent
Olesen

(10) Patent No.: US PP23,604 P3
(45) Date of Patent: May 21, 2013

(54) MINIATURE ROSE PLANT NAMED 'POULPAR058'

(50) Latin Name: ***Rosa* hybrid**
Varietal Denomination: Poulpar058

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 13 days.

(21) Appl. No.: 13/317,243

(22) Filed: Oct. 13, 2011

(65) Prior Publication Data

US 2013/0097745 P1 Apr. 18, 2013

(51) Int. Cl.
*A01H 5/00* (2006.01)

(52) U.S. Cl.
USPC ..... Plt./121; Plt./116

(58) Field of Classification Search
USPC ..... Plt./116, 121
See application file for complete search history.

*Primary Examiner* — Susan McCormick Ewoldt

(57) ABSTRACT

A new miniature rose plant that has abundant, mauve flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar058'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2005 and the resulting seeds were planted in a controlled environment in Fredensborg, Denmark. The new variety, named 'Poulpar058', originated as a single seedling from the stated cross.

The new variety may be distinguished from its female seed parent primarily by flower color. The female seed parent has pink flowers while the new variety has mauve flowers.

The new variety may be distinguished from its male pollen parent primarily by the growth habit. The male pollen parent is is taller, about 25 cm in height, while the new variety is more compact, about 19 cm in height.

The objective of the hybridization of this rose variety for commercial culture was to create a new and distinct variety with unique qualities, such as:

1. Uniform and abundant mauve flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar058' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpar058' was selected by the inventor as a single plant from the progeny of the hybridization in 2005.

Asexual reproduction of 'Poulpar058' by cuttings and traditional budding was first done by Mogens N. Olesen in the nursery in Fredensborg, Denmark in June of 2006. This initial and other subsequent propagations conducted in controlled environments have demonstrated that the characteristics of 'Poulpar058' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar058'.

DETAILED DESCRIPTION OF THE VARIETY

The following is a description of 'Poulpar058', as observed in its growth in glasshouses in Burlington, Ontario, Canada. Observed plants are 3 months of age and were cultivated in 15 cm pots. Color references are made using The Royal Horticultural Society (London, England) Colour Chart, 2001, except where common terms of color are used.

For a comparison, several physical characteristics of the rose variety 'Poulpar034', U.S. Plant Pat. No. 16,582. are compared to 'Poulpar058' in Chart 1.

CHART 1

| | 'Poulpar058' | 'Poulpar034' |
|---|---|---|
| Petalage: | 18 to 20 | 55 petals |
| Flower Diameter: | 42 mm | 35 to 40 mm |
| General Tonality of Flower Color: | Purple Group 75A | Purple Group 75D |

FLOWER AND FLOWER BUD

Blooming habit: Continuous.

Flower bud:

*Size*.—Upon opening, 20 mm in length from base of receptacle to end of bud. 10 mm in diameter.

*Bud form*.—Ovate.

*Bud color*.—As sepals unfold, petals are Purple Group 75B.

*Sepals*.—Upper Surface: Color: Green Group 138B. Texture: Moderately pubescent. Lower Surface: Color: Yellow-Green Group 144A. Texture: Smooth. Shape: Apex: Cirrhose. Base: Flat at union with receptacle. Margins: Margins have weak foliaceous appendages on three of the five sepals. Size: 20 mm long by 5 mm wide.

*Receptacle*.—Surface Texture: Smooth. Shape: Campanulate. Size: 5 mm in height by 6 mm wide. Color: Yellow-Green Group 144A.

*Pedicel*.—Surface: Smooth. Length: 35 mm average length. Diameter: 2 mm. Color: Yellow-Green Group 144A. Strength: Medium strength. Borne: Singly.

Flower bloom:

*Fragrance*.—None.

*Duration*.—As a pot plant, flowers last up to 28 days. Petals do not fall cleanly away from plant.

*Size*.—Average flower diameter is 42 mm when open.

*Form*.—Flowers are initially high centered, similar to a hybrid tea rose. Afterward, petals fully open to expose the flower parts.

*Shape of flower, side view*.—Upper portion is flat, while the lower portion is a flattened convex.

Petalage: There are normally 18 to 20 petals, 1 to 2 of which are petaloids.

Color:

*Upon opening, petals*.—Outermost petals: Upper Surface: Purple Group 75A. Lower Surface: Purple Group 75B with a streak up the center Purple Group 75D. Innermost petals: Upper Surface: Purple Group 75A. Lower Surface: Purple Group 75B.

*Upon opening, basal petal spots*.—Yellow-Green Group 149D on the upper and lower surface.

*After opening, petals*.—Outermost petals: Upper Surface: Purple Group 75B. Lower Surface: Purple Group 75C with marginal intonations of Purple Group 75B.

*After opening, basal petal spots*.—Yellow-Green Group 149D on the upper and lower surface.

General tonality: On open flower Purple Group 75A. After 7 days the color is Purple Group 75B.

Petals:

*Petal reflex*.—Weak.

*Petal margin*.—Entire with a point in the center. No undulations in the margin.

*Shape*.—Generally round. Base: Round. Apex: Round.

*Size*.—On average, 20 mm in length by 20 mm wide.

*Thickness*.—Average.

Petaloids:

*Quantity*.—Normally, there are 1 or 2.

*Size*.—7 mm long; 5 mm wide.

*Shape*.—Apex is acute. Base is acute. Generally the petaloids are elliptic.

*Petaloid color*.—Upper Surface: Purple Group 75B. Lower Surface: Purple Group 75C with marginal intonations of Purple Group 75B. Petaloid spots: Yellow-Green Group 149D on the upper and lower surface.

Reproductive organs:

*Pollen*.—None observed.

*Anthers*.—Size: 2 mm long. Color: Yellow-Orange Group 22A. Quantity: About 45.

*Filaments*.—Color: Yellow Group 11D. Length: 3 mm.

*Pistils*.—Length: 3 mm long. Quantity: About 15.

*Stigmas*.—Level relative to the length of the filaments and the height of the anthers. Color: Orange-White Group 159C.

*Styles*.—Color: Green-White Group 157C and Red Group 43C.

*Seed formation*.—Not observed.

PLANT

Plant growth: Upright. When grown as a 10.5 cm pot on its own roots, the average height of the plant itself is 19 cm and the average width is 15 cm.

Stems:

*Color*.—Young wood: Yellow-Green Group 144B. Older wood: Yellow-Green Group 144A.

*Internodal distance*.—15 to 20 mm.

*Length and width*.—From the base of the plant to the flowering portion is 13 cm. The diameter is 3 mm on average.

*Surface texture*.—Young wood: Smooth. Older wood: Smooth.

Prickles: None. Observed plants are without prickles.

Plant foliage: Normal number of leaflets on normal leaves in middle of the stem: 5 leaflets.

*Compound leaf size*.—60 mm (l)×45 mm (w).

*Quantity*.—4 leaves per 10 cm of stem.

*Color*.—Juvenile foliage: Upper Leaf Surface: Yellow-Green Group 144A to 146B. Lower Leaf Surface: Yellow-Green Group 147C. Anthocyanin: Greyed-Purple Group 183A on the leaflet margins. Mature foliage: Upper Leaf Surface: Yellow-Green Group 147A. Lower Leaf Surface: Yellow-Green Group 147B.

Plant leaves and leaflets:

*Stipules*.—Size: 5 mm in length. Shape: Linear, slightly broad based with outward extending apices. Margins: Entire. Color: Yellow-Green Group 144A.

*Petiole*.—Length: 13 mm long by 1 mm wide. Color: Upper surface is Green Group 137A. Lower surface is Yellow-Green Group 144A. Underneath: Many minute stipitate glands.

*Rachis*.—Size: About 15 mm long. Color: Upper surface is Green Group 137A. Lower surface is Yellow-Green Group 144A. Underneath: Many minute stipitate glands

*Leaflet*.—Size: Terminal leaflets are 25 mm length by 18 mm wide on average. Margin: Doubly serrate. General Shape: Elliptical. Apex Shape: Acute. Base Shape: Round. Texture: Smooth. Arrangement: Odd pinnate. Venation: Reticulate. Leaf Gloss: Matte finish.

Disease resistance: Average resistance to powdery and downy mildew, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar058', substantially as illustrated and described herein, due to its abundant, mauve flowers, vigorous growth, compact habit, suitability for production from softwood cuttings in pots, and durable flowers and foliage that make the variety suitable for distribution in the floral industry.

* * * * *

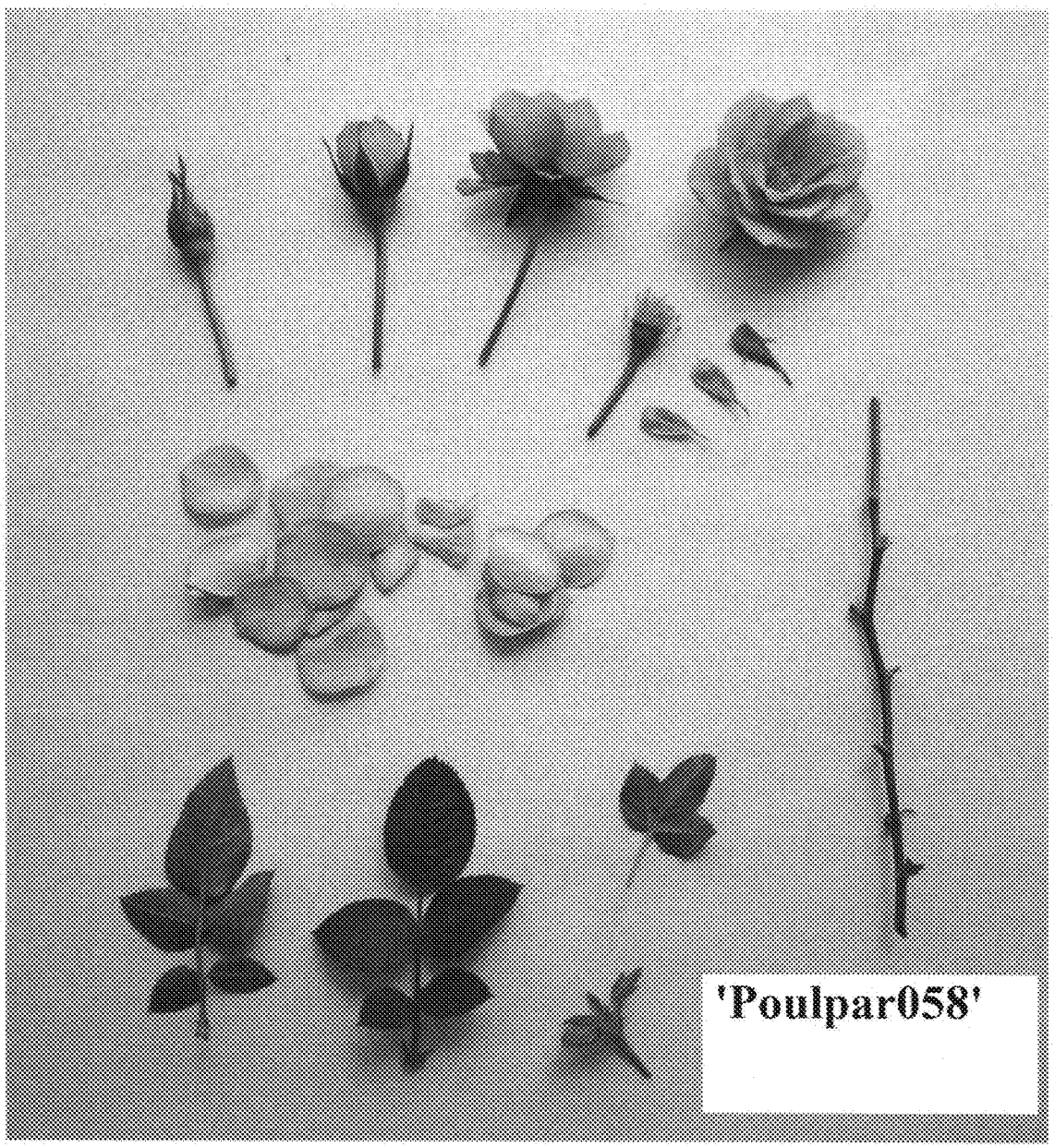
'Poulpar058'